United States Patent
Schur et al.

(10) Patent No.: US 9,615,849 B2
(45) Date of Patent: *Apr. 11, 2017

(54) CUTTING WIRE ASSEMBLY FOR USE WITH A CATHETER

(71) Applicants: Israel Schur, Teaneck, NJ (US); Rex Medical, L.P., Conshohocken, PA (US)

(72) Inventors: Israel Schur, Teaneck, NJ (US); James F. McGuckin, Jr., Radnor, PA (US); James Erich Bressler, Langhorne, PA (US)

(73) Assignee: Rex Medical, L.P., Conshohocken, PA (US)

( * ) Notice: Subject to any disclaimer, the term of this patent is extended or adjusted under 35 U.S.C. 154(b) by 2 days.

This patent is subject to a terminal disclaimer.

(21) Appl. No.: 14/738,856

(22) Filed: Jun. 13, 2015

(65) Prior Publication Data

US 2015/0272613 A1   Oct. 1, 2015

Related U.S. Application Data

(60) Continuation of application No. 14/181,657, filed on Feb. 15, 2014, now abandoned, which is a division of
(Continued)

(51) Int. Cl.
*A61B 17/22* (2006.01)
*A61B 17/3207* (2006.01)

(52) U.S. Cl.
CPC ............ *A61B 17/320725* (2013.01); *A61B 2017/22001* (2013.01); *A61B 2017/22038* (2013.01); *A61B 2017/22051* (2013.01)

(58) Field of Classification Search
CPC ...... A61M 25/00; A61M 25/10; A61M 29/00; A61B 17/32; A61B 17/3207;
(Continued)

(56) References Cited

U.S. PATENT DOCUMENTS 5,158,564 A   10/1992   Schnepp-pesch
5,176,693 A    1/1993   Pannek, Jr.
(Continued)

FOREIGN PATENT DOCUMENTS

WO   WO-98/19608      5/1998
WO   WO-2004/041329   5/2004
(Continued)

OTHER PUBLICATIONS

EP-11 18 3669—European Search Report. Date of completion of the search, Jan. 23, 2012.

*Primary Examiner* — Ashley Fishback
(74) *Attorney, Agent, or Firm* — Neil D. Gershon

(57) ABSTRACT

A method of treating a lesion in a body lumen to enlarge a passageway in the lumen including inserting a plurality of cutting members and a tracking member through a first lumen of a catheter, withdrawing the catheter from the cutting members and tracking member, inserting the catheter over the tracking member and leaving the cutting members outside the catheter, and expanding a portion of the catheter to move the cutting members into cutting contact with the lesion. A device for treating a lesion in a body lumen including a plurality of cutting members and a tracking member is also provided.

12 Claims, 5 Drawing Sheets

Related U.S. Application Data application No. 13/226,699, filed on Sep. 7, 2011, now Pat. No. 8,685,049.

(60) Provisional application No. 61/414,931, filed on Nov. 18, 2010.

(58) Field of Classification Search
CPC .. A61B 17/320725; A61B 2017/22001; A61B 2017/22038; A61B 2017/22051
See application file for complete search history.

(56) References Cited

U.S. PATENT DOCUMENTS

| | | |
|---|---|---|
| 5,196,024 A | 3/1993 | Barath |
| 5,211,651 A | 5/1993 | Reger |
| 5,282,484 A | 2/1994 | Reger |
| 5,320,634 A | 6/1994 | Vigil |
| 5,431,673 A | 7/1995 | Summers |
| 5,527,326 A | 6/1996 | Hermann |
| 5,549,552 A | 8/1996 | Peters et al. |
| 5,554,163 A | 9/1996 | Shturman |
| 5,556,408 A | 9/1996 | Farhat |
| 5,616,149 A | 4/1997 | Barath |
| 5,628,746 A | 5/1997 | Clayman |
| 5,658,301 A | 8/1997 | Lemaitre |
| 5,665,098 A | 9/1997 | Kelly |
| 5,697,944 A | 12/1997 | Lary |
| 5,728,123 A | 3/1998 | Lemelson |
| 5,772,676 A | 6/1998 | Cuschieri |
| 5,797,935 A | 8/1998 | Barath |
| 5,897,567 A | 4/1999 | Ressemann |
| 5,904,679 A | 5/1999 | Clayman |
| 5,941,869 A | 8/1999 | Patterson |
| 6,022,362 A | 2/2000 | Lee |
| 6,027,514 A | 2/2000 | Stine |
| 6,036,708 A | 3/2000 | Sciver |
| 6,156,043 A | 12/2000 | Krahn |
| 6,165,187 A | 12/2000 | Reger |
| 6,165,195 A | 12/2000 | Wilson |
| 6,210,380 B1 | 4/2001 | Mauch |
| 6,221,090 B1 | 4/2001 | Wilson |
| 6,264,667 B1 | 7/2001 | McGuckin, Jr. |
| 6,361,544 B1 | 3/2002 | Wilson |
| 6,387,108 B1 | 5/2002 | Taylor |
| 6,394,995 B1 | 5/2002 | Solar |
| 6,440,147 B1 | 8/2002 | Lee |
| 6,447,501 B1 | 9/2002 | Solar |
| 6,475,222 B1 | 11/2002 | Berg |
| 6,494,875 B1 | 12/2002 | Mauch |
| 6,508,836 B2 | 1/2003 | Wilson |
| 6,565,588 B1 | 5/2003 | Clement |
| 6,632,231 B2 | 10/2003 | Radisch, Jr. |
| 6,702,831 B2 | 3/2004 | Lee |
| 6,740,104 B1 | 5/2004 | Solar |
| 6,746,463 B1 | 6/2004 | Schwartz |
| 6,780,174 B2 | 8/2004 | Mauch |
| 6,780,179 B2 | 8/2004 | Lee |
| 6,780,199 B2 | 8/2004 | Solar |
| 6,796,989 B2 | 9/2004 | Uflacker |
| 6,808,531 B2 | 10/2004 | Lafontaine |
| 6,824,551 B2 | 11/2004 | Trerotola |
| 6,835,059 B2 | 12/2004 | Skinner |
| 6,872,204 B2 | 3/2005 | Houser |
| 6,942,680 B2 | 9/2005 | Grayzel |
| 6,951,566 B2 | 10/2005 | Lary |
| 7,008,434 B2 | 3/2006 | Kurz |
| 7,008,438 B2 | 3/2006 | O'Brien |
| 7,029,450 B2 | 4/2006 | Gellman |
| 7,070,576 B2 | 7/2006 | O'Brien |
| 7,131,981 B2 | 11/2006 | Appling et al. |
| 7,147,631 B2 | 12/2006 | Scopton |
| 7,153,315 B2 | 12/2006 | Miller |
| 7,172,609 B2 | 2/2007 | Radisch, Jr. |
| 7,179,024 B2 | 2/2007 | Greenhalgh |
| 7,252,674 B2 | 8/2007 | Wyzgala |
| 7,270,673 B2 | 9/2007 | Yee |
| 7,279,002 B2 | 10/2007 | Shaw |
| 7,291,158 B2 | 11/2007 | Crow |
| 7,294,117 B2 | 11/2007 | Provost-tine |
| 7,303,572 B2 | 12/2007 | Melsheimer |
| 7,329,267 B2 | 2/2008 | Weber |
| 7,344,546 B2 | 3/2008 | Wulfman |
| 7,396,358 B2 | 7/2008 | Appling |
| 7,399,307 B2 | 7/2008 | Evans |
| 7,416,555 B2 | 8/2008 | Krivoruchko |
| 7,479,153 B2 | 1/2009 | Belef |
| 7,494,497 B2 | 2/2009 | Weber |
| 7,517,352 B2 | 4/2009 | Evans |
| 7,632,288 B2 | 12/2009 | Wu |
| 7,637,885 B2 | 12/2009 | Maschke |
| 7,648,502 B2 | 1/2010 | Jacques |
| 7,658,744 B2 | 2/2010 | Jackson |
| 7,662,163 B2 | 2/2010 | Grayzel |
| 7,691,116 B2 | 4/2010 | Goodin |
| 7,734,332 B2 | 6/2010 | Sher |
| 7,736,375 B2 | 6/2010 | Crow |
| 7,753,907 B2 | 7/2010 | Dimatteo |
| 7,754,047 B2 | 7/2010 | Kelley |
| 7,758,604 B2 | 7/2010 | Wu |
| 7,771,447 B2 | 8/2010 | Kunis |
| 7,780,626 B2 | 8/2010 | Wu |
| 7,799,043 B2 | 9/2010 | O'Brien |
| 7,833,223 B2 | 11/2010 | Vakharia |
| 7,862,575 B2 | 1/2011 | Tal |
| 7,883,537 B2 | 2/2011 | Grayzel |
| 7,887,557 B2 | 2/2011 | Kelley |
| 7,901,378 B2 | 3/2011 | Solar |
| 7,919,910 B2 | 4/2011 | Eidenschink |
| 7,955,350 B2 | 6/2011 | Konstantino |
| 7,985,234 B2 | 7/2011 | Wang |
| 8,070,729 B2 | 12/2011 | Solar |
| 8,080,026 B2 | 12/2011 | Konstantino |
| 8,348,987 B2 | 1/2013 | Eaton |
| 2003/0055444 A1 | 3/2003 | Evans |
| 2003/0163148 A1 | 8/2003 | Wang |
| 2003/0195546 A1 | 10/2003 | Solar |
| 2003/0208219 A1 | 11/2003 | Aznoian |
| 2004/0087876 A1 | 5/2004 | Eskuri |
| 2004/0122458 A1 | 6/2004 | Opie |
| 2004/0133148 A1 | 7/2004 | Jacques |
| 2004/0193196 A1 | 9/2004 | Appling et al. |
| 2004/0199088 A1 | 10/2004 | Bakos |
| 2005/0085836 A1 | 4/2005 | Raymond |
| 2005/0119678 A1 | 6/2005 | O'Brien |
| 2005/0137615 A1 | 6/2005 | Mapes |
| 2005/0197593 A1 | 9/2005 | Burbank |
| 2005/0209617 A1 | 9/2005 | Koven |
| 2005/0240148 A1 | 10/2005 | Cheves |
| 2005/0288629 A1 | 12/2005 | Kunis |
| 2006/0085026 A1 | 4/2006 | Appling et al. |
| 2006/0111736 A1 | 5/2006 | Kelley |
| 2006/0116700 A1 | 6/2006 | Crow |
| 2006/0116701 A1 | 6/2006 | Crow |
| 2006/0178685 A1 | 8/2006 | Melsheimer |
| 2006/0206125 A1 | 9/2006 | Fogarty |
| 2007/0016232 A1 | 1/2007 | St. Martin |
| 2007/0233163 A1 | 10/2007 | Bombard |
| 2007/0250096 A1 | 10/2007 | Yamane |
| 2007/0270893 A1 | 11/2007 | Pikus |
| 2008/0045987 A1 | 2/2008 | Lee |
| 2008/0077164 A1 | 3/2008 | Murphy |
| 2008/0077165 A1 | 3/2008 | Murphy |
| 2008/0147103 A1 | 6/2008 | Shekalim |
| 2008/0215077 A1 | 9/2008 | Sepetka |
| 2008/0228208 A1 | 9/2008 | Wulfman |
| 2008/0249552 A1 | 10/2008 | Eliachar |
| 2008/0255595 A1 | 10/2008 | Buchbinder |
| 2008/0255596 A1 | 10/2008 | Jenson |
| 2008/0269789 A1 | 10/2008 | Eli |
| 2008/0306499 A1 | 12/2008 | Katoh |
| 2009/0012548 A1 | 1/2009 | Thatcher |
| 2009/0099581 A1 | 4/2009 | Kim |
| 2009/0105686 A1 | 4/2009 | Snow |
| 2009/0125044 A1 | 5/2009 | Lary |

(56) References Cited

U.S. PATENT DOCUMENTS

| | | |
|---|---|---|
| 2009/0306582 A1 | 12/2009 | Granada |
| 2010/0010521 A1 | 1/2010 | Kurrus |
| 2010/0023035 A1 | 1/2010 | Kontos |
| 2010/0057077 A1 | 3/2010 | Ducharme |
| 2010/0094259 A1 | 4/2010 | Makower |
| 2010/0094320 A1 | 4/2010 | Arat |
| 2010/0121361 A1 | 5/2010 | Plowe |
| 2010/0125266 A1 | 5/2010 | Deem |
| 2010/0137893 A1 | 6/2010 | Kilemnick |
| 2010/0198191 A1 | 8/2010 | Clifford |
| 2010/0234864 A1 | 9/2010 | Keller |
| 2010/0286720 A1 | 11/2010 | Shaked |
| 2011/0034949 A1 | 2/2011 | Solar |
| 2011/0071559 A1 | 3/2011 | Holman |
| 2011/0087257 A1 | 4/2011 | To |
| 2011/0118774 A1 | 5/2011 | Solar |
| 2011/0125132 A1 | 5/2011 | Krolik et al. |
| 2011/0125172 A1 | 5/2011 | Gelbart |
| 2011/0160645 A1 | 6/2011 | Sutermeister et al. |

FOREIGN PATENT DOCUMENTS

| | | |
|---|---|---|
| WO | WO-2010/002549 | 1/2010 |
| WO | WO-2010/003135 | 1/2010 |
| WO | WO-2010/011956 | 1/2010 |

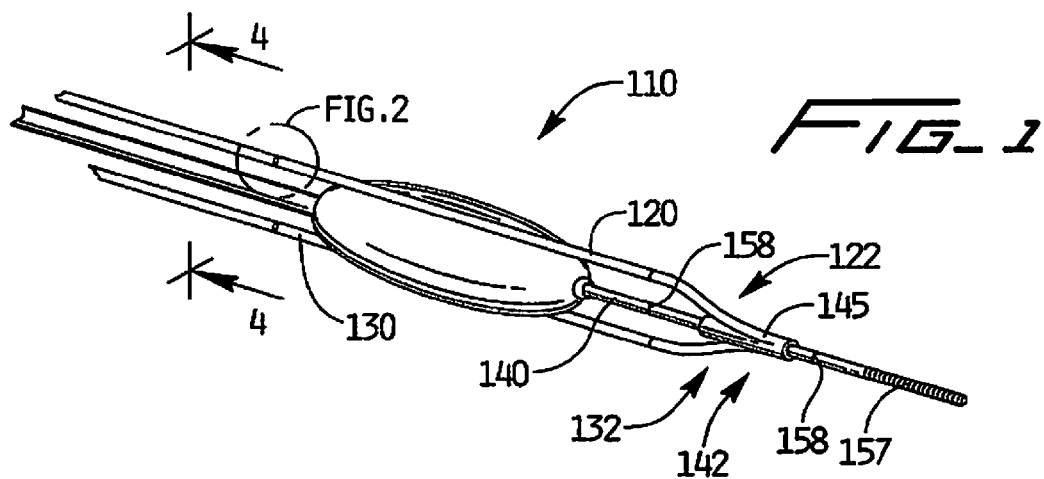
FIG_1
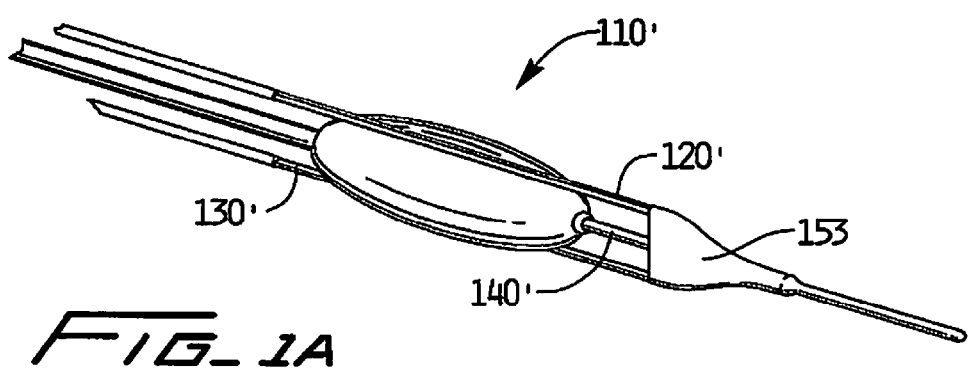
FIG_1A
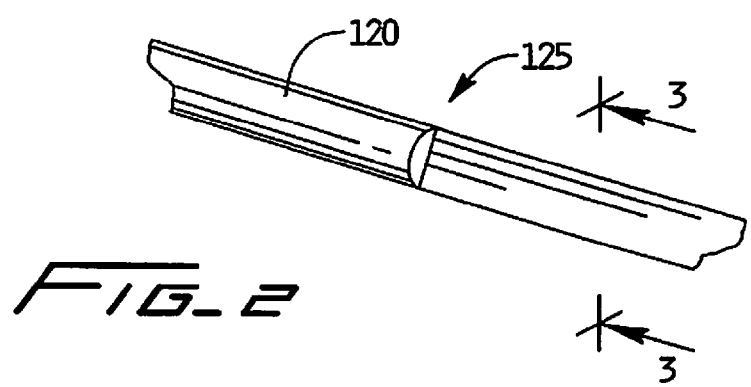
FIG_2

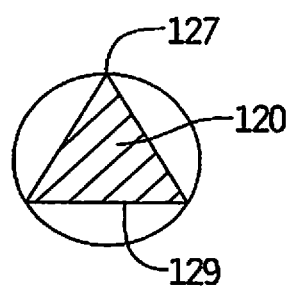
FIG_3
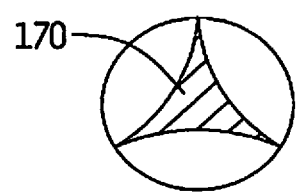
FIG_3A
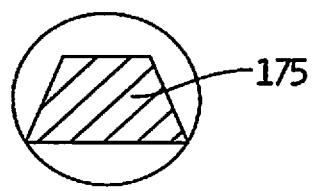
FIG_3B
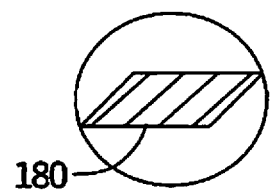
FIG_3C
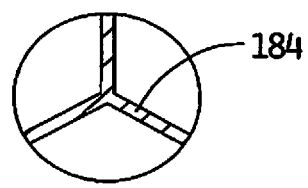
FIG_3D
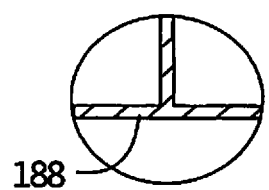
FIG_3E

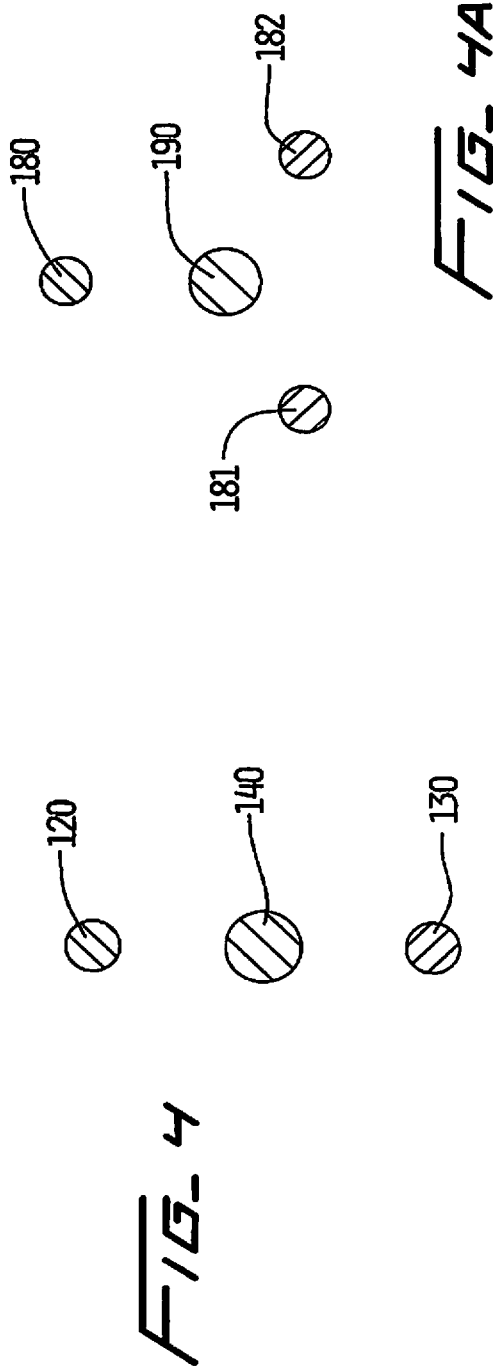
FIG. 4
FIG. 4A
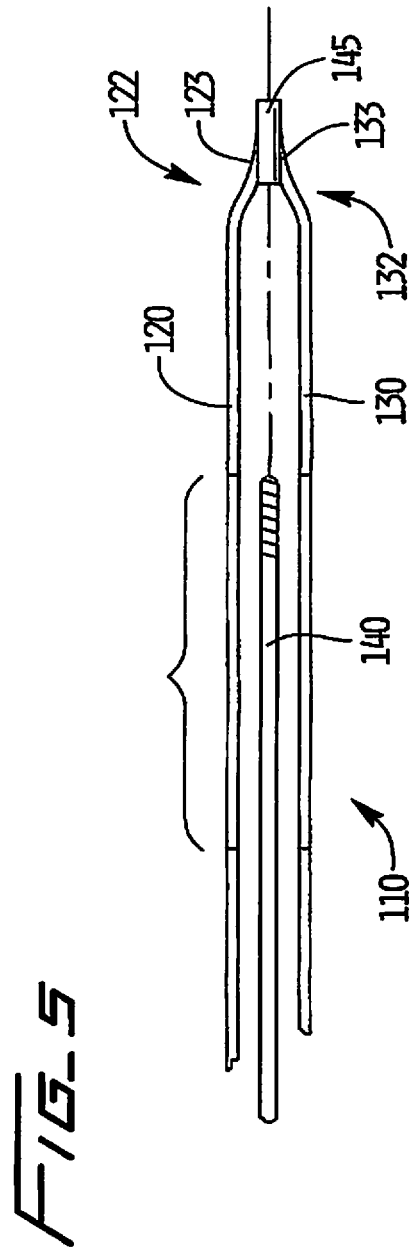
FIG. 5

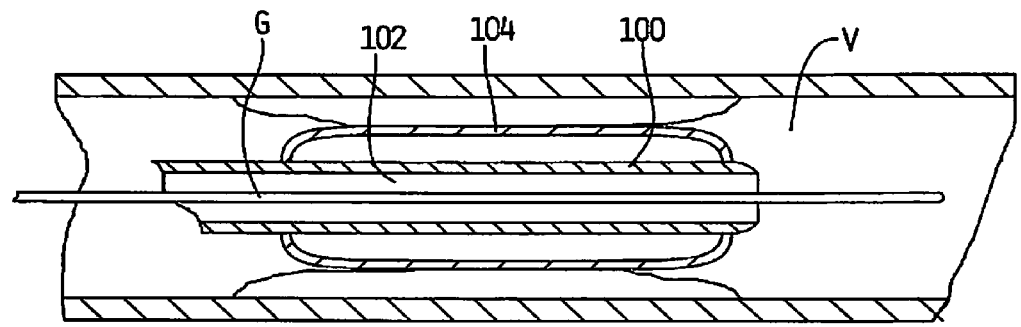
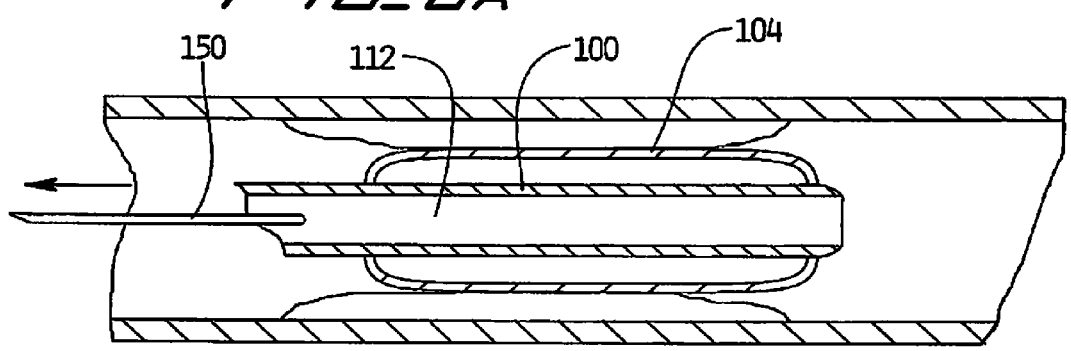
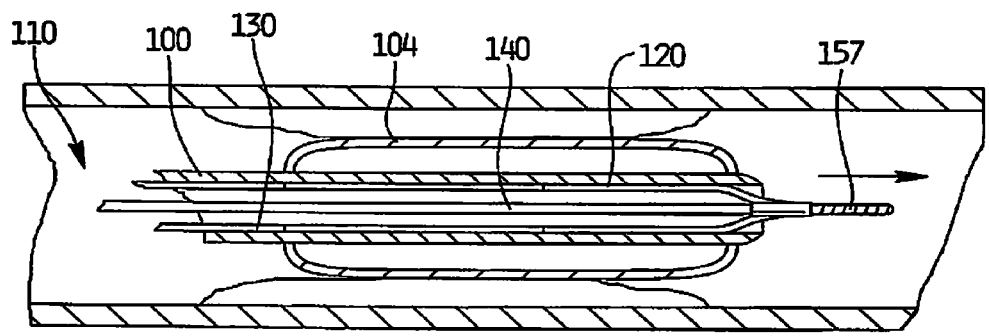

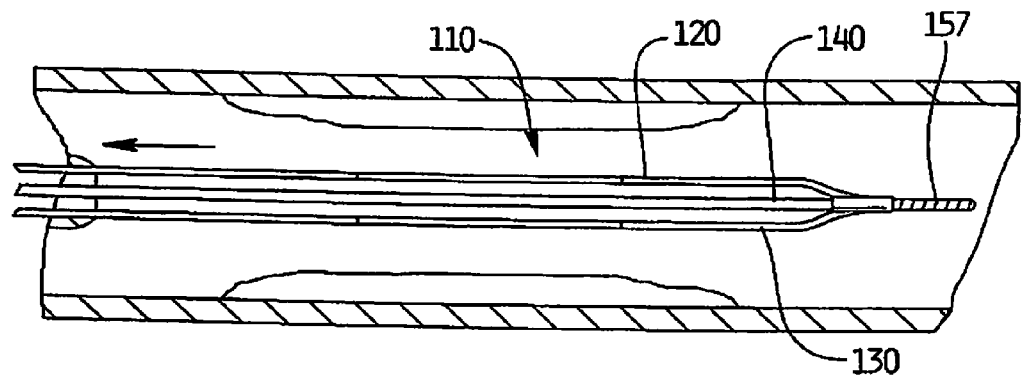
FIG_6C
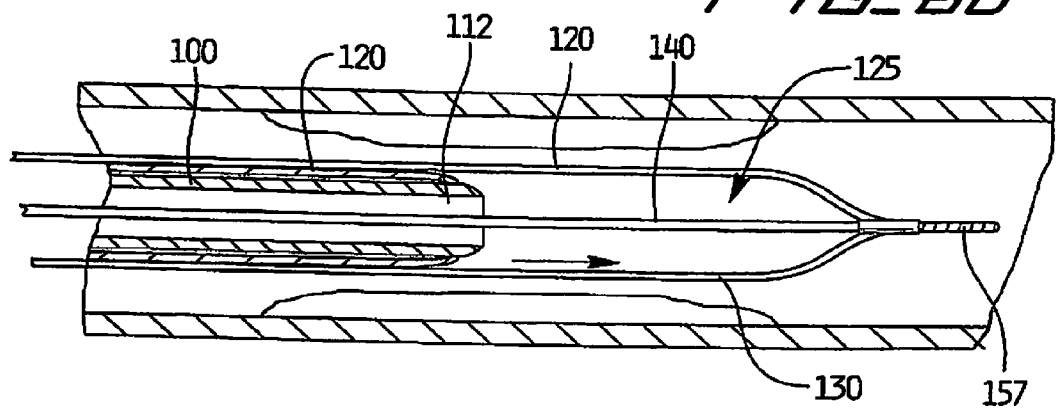
FIG_6D
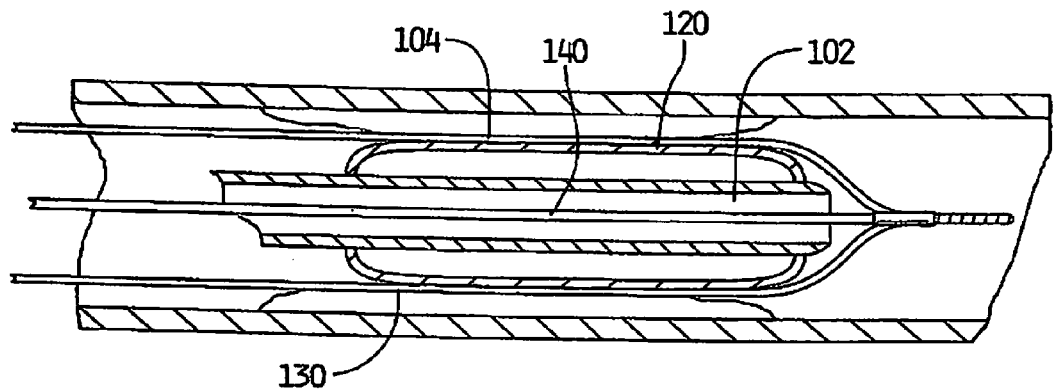
FIG_6E

CUTTING WIRE ASSEMBLY FOR USE WITH A CATHETER

This application is a continuation of co-pending U.S. application Ser. No. 14/181,657, filed Feb. 15, 2014, which is a divisional of U.S. application Ser. No. 13/226,699, filed Sep. 7, 2011, now U.S. Pat. No. 8,685,049, which claims priority from provisional application Ser. No. 61/414,931, filed Nov. 18, 2010. The entire contents of each of these applications are incorporated herein by reference.

BACKGROUND

Technical Field

This application relates to a system and method for treating stenotic lesions of a vessel and more particularly relates to cutting wires for use with a catheter to open stenotic lesions in vessels.

Background of Related Art

Several methods have been utilized to treat stenotic lesions of vessels. With stenotic lesions, the vessel diameter is constricted and therefore attempts have been made to widen this constriction. One method is an invasive surgical procedure where the vessel wall is cut open and the portion containing the plaque or other constricting structure is removed. This procedure is traumatic, complex, and results in a long recovery time for the patient. It also causes a weakening of the vessel wall since a portion of the wall is removed. A weakened wall can ultimately result in an aneurysm which is a dilatation (expansion) of the artery, which adversely affects vessel function and if not surgically treated could be life threatening to the patient.

In order to reduce trauma to the patient, reduce the patient recovery time and reduce hospital costs, minimally invasive procedures have been developed to treat stenotic lesions. Balloon angioplasty is one such method. In angioplasty, a balloon is placed in the stenosed (restricted) portion of the vessel and inflated to compress the plaque against the vessel wall, thereby increasing the lumen in the vessel to improve blood flow. That is, the balloon is inflated to push the lesion radially outwardly to widen the passageway. Some stenotic lesions are resistant to conventional pressure balloons. Consequently, high pressure balloons have been developed to treat resistant stenotic lesions. However, such high pressure balloons apply more force and increase the risk of vessel trauma and rupture. Moreover, sometimes lesions are even resistant to these high pressure balloons.

Additionally, the use of these angioplasty balloon catheters oftentimes have only short term effect as it has been found that restenosis frequently occurs after such treatment.

In an attempt to address such drawbacks as reducing the likelihood of restenosis, and trauma, as well as to treat vessels with highly resistant lesions, cutting balloon catheters were developed. One such device is disclosed for example in U.S. Pat. No. 5,196,024 which describes a catheter with a balloon and longitudinal cutting edges. One of the many disadvantages of this device, however, is it requires modifications of balloon catheters which significantly increases the cost of the catheter. Another disadvantage is that instead of using the procedural catheter, a different catheter may be required with a cutting balloon. Consequently, the surgeon would need to decide prior to the procedure which type of catheter to utilize, although this may not always be practical as the information to determine the type (e.g. resistance) of the lesion may not be available until the lesion is accessed and the extent of the disease is known. Thus, for example, the surgeon may insert an angioplasty catheter, inflate the balloon and find that it is insufficient to widen the vessel passageway. The surgeon would then need to conduct the time consuming task of removing the catheter and inserting a cutting balloon catheter, threading it through the vascular system over a guidewire. Since the catheters are inserted from a remote site, e.g. through the femoral artery, these catheter exchanges take time and increase trauma to the patient. Additionally, it adds to the cost of the procedure since two catheters would be required. In order to properly treat the diverse size and condition of each lesion, a large inventory of multiple sized cutting balloons would be required.

Conversely, in certain procedures, utilizing a cutting balloon in soft lesions increases the risk of trauma or damage to the vessel and therefore it would not be desirable to use a cutting balloon catheter. Thus, an exchange for an angioplasty catheter would be necessary.

Such catheter exchanges might also require guidewire exchanges since the standard 0.035" guidewire utilized for an angioplasty catheter may be too large for the 0.018" cutting balloon catheter. The guidewire exchanges complicate the procedure, increase the risk to the patient and increase the procedure time, thereby increasing costs to the patient.

U.S. Pat. No. 7,131,981 attempts to address the foregoing issues by providing a conversion device comprising an insertion tube insertable into the normal 0.035" guidewire lumen of an angioplasty catheter. This device would not work for angioplasty catheters with small guidewire lumens. The tube has two jacket segments and a guide insert device having a channel and four guide channels. Because of the complexity of the device, the cutting elements in the four channels would need to be sufficiently thin to be maintained in the smaller diameter device. Such thin (small diameter) cutting elements however may be too flexible and not have adequate stiffness to be effective. Additionally, the cutting elements are attached at one end, having an opposite free end which can potentially damage and perforate the vessel wall during use.

The need therefore exists for an improved, more simplified device and method to enable the selective use of a cutting wire for treating stenosis.

SUMMARY

The present invention overcomes the disadvantages and deficiencies of the prior art.

In one aspect, the present invention provides a method of treating a lesion in a body lumen comprising inserting a plurality of cutting members and a tracking member through a first lumen of a catheter, withdrawing the catheter from the cutting members and tracking member, inserting the catheter over the tracking member while leaving the cutting members outside the catheter, and expanding a portion of the catheter to move the cutting members into cutting contact with the lesion to enlarge a passageway in the body lumen.

In some embodiments, the step of inserting a catheter over the tracking member comprises reinserting the same catheter through which the cutting members and tracking member were initially inserted. In other embodiments a different catheter is utilized.

The catheter preferably includes an expandable balloon, and the step of expanding the catheter preferably includes the step of expanding a portion of the balloon to cause the cutting members to be moved radially with respect to the catheter. Preferably, the step of expanding a portion of the catheter causes a gap between the cutting members and tracking member to widen.

In some embodiments, each of the cutting members has a cutting edge opposite an edge facing the tracking member, and expansion of a portion of the catheter forces the cutting edges into diseased narrowed sections within the lesion.

In preferred embodiments, the cutting members and tracking member are attached at their distal ends and inserted as a unit through the lumen of the catheter.

In some embodiments, the length of the tracking member can exceed the length of the cutting members.

In some embodiments, the cutting members have a first portion of a first configuration and a second portion of a second configuration, the second portion including a cutting surface and the first portion being atraumatic. A height of the second portion can be less than a height of the first portion.

The tracking member can have a coil at a distal tip. Marker bands can be provided on the tracking member.

In another aspect, the present invention provides a method of treating a lesion in a body lumen to enlarge a passageway in the body lumen comprising inserting a plurality of cutting members and a tracking member into the vessel, inserting a catheter over the tracking member so the tracking member extends through a first lumen of the catheter and the cutting members do not extend through the first lumen, and moving the cutting members away from the tracking member into cutting contact with the lesion to enlarge the passageway in the body lumen.

Preferably, the step of inserting the cutting members and tracking member comprises the step of inserting the cutting members and tracking member through a lumen of a catheter.

In some embodiments, the catheter through which the cutting and tracking members are initially inserted is the same catheter subsequently inserted over the tracking member. In other embodiments a different catheter is utilized. In some embodiments, the step of moving the cutting members comprises the step of expanding a balloon of the catheter. In preferred embodiments, the cutting members and tracking member are wires and are attached at their distal end and inserted as a unit into the vessel.

In some embodiments, the cutting member is substantially circular in cross-section in a proximal region and substantially triangular in a distal region.

In another aspect, the present invention provides a device for treating a lesion in a body lumen to enlarge a passageway in a body lumen comprising a plurality of cutting members having a proximal portion and a distal portion and a tracking member having a proximal portion and distal portion. The cutting members and tracking member are connected at their distal portions and insertable into the vessel as a unit, the cutting members configured for movement in a direction transverse to a longitudinal axis of the tracking member to widen a gap between the cutting members and tracking member at least at a distal region.

In some embodiments, the cutting members each have a cutting surface on a first surface opposite a second surface facing the tracking member. In some embodiments, the cutting members have a cutting surface with a flat edge on an edge opposite a surface facing the tracking member. The surface opposite the cutting surface can have a convex surface. In some embodiments, the tracking member and cutting members are connected by twisting of the members at the distal portion.

In some embodiments, the tracking member has a coil at a distal end. A shrink wrap can be positioned over a connection region of the cutting members and tracking member. The tracking member can include a plurality of marker bands.

In some embodiments, the cutting surface is formed only in a distal region of the cutting members.

In another aspect, the present invention provides a system for treating lesions in a body lumen to enlarge a restriction in the body lumen comprising a catheter having a lumen and an expandable portion and a cutting assembly including a plurality of cutting members and a tracking member, the tracking member attached to at least one of the cutting members. The expandable portion of the catheter is expandable to move the cutting members in a direction transverse to a longitudinal axis of the tracking member, the cutting members having a cutting surface configured to treat the lesion to enlarge a passageway in the body lumen when moved by the expandable portion of the catheter.

In some embodiments, the cutting members and tracking member are connected at distal regions thereof. In some embodiments, the expandable portion comprises an inflatable balloon.

The tracking member can have a coil at a distal end. A shrink wrap can be positioned over a connection region of the cutting members and tracking member.

BRIEF DESCRIPTION OF THE DRAWINGS

Preferred embodiment(s) of the present invention are described herein with reference to the drawings wherein:

FIG. 1 is a perspective view of a conventional balloon catheter and the cutting wire assembly (unit) of the present invention showing the balloon expanded;

FIG. 1A is perspective view of an alternate embodiment of the cutting wire assembly;

FIG. 2 is a perspective view of the area of detail of FIG. 1 showing a portion of the cutting wire in accordance with one embodiment;

FIG. 3 is a cross-sectional view of the cutting wire taken along line 3-3 of FIG. 2;

FIGS. 3A-3E are views similar to FIG. 3 showing cross-sectional views of alternate embodiments of the cutting wire of the present invention;

FIG. 4 is a cross-sectional view taken along line 4-4 of FIG. 1;

FIG. 4A is a cross-sectional view of another embodiment of the cutting wire assembly of the present invention;

FIG. 5 is a partially exploded side view of the cutting wire assembly of FIG. 1;

FIGS. 6-6E illustrate the method steps for use of the cutting wire assembly of FIG. 1, the drawings showing cross-sectional views, wherein:

FIG. 6 illustrates a conventional balloon catheter inserted over a conventional guidewire;

FIG. 6A illustrates withdrawal of the conventional guidewire;

FIG. 6B illustrates insertion of the cutting and tracking elements of the present invention through the balloon catheter lumen;

FIG. 6C illustrates withdrawal of the balloon catheter;

FIG. 6D illustrates the balloon catheter inserted over the tracking element; and FIG. 6E illustrates expansion of the balloon of the balloon catheter to force the cutting elements into cutting contact with the lesion.

DETAILED DESCRIPTION OF PREFERRED EMBODIMENTS

Referring now in detail to the drawings wherein like reference numerals identify similar or like components throughout the several views, the cutting assembly of the present invention includes a plurality of cutting members (or elements) and a tracking member (or element). More specifically, cutting assembly includes, an assembly 110 having a tracking member, designated generally by reference numeral 140, preferably in the form of a wire, and two cutting members, designated generally by reference numerals 120 and 130, and preferably in the form of wires. As discussed in more detail below, the tracking wire 140 and cutting wires 120, 130 are preferably attached at a distal portion so they are insertable as a unit. The wire assembly 110, as described below, can be used with a conventional catheter, such as an angioplasty catheter. Additionally, although two cutting wires are shown in FIG. 1, spaced about 180 degrees apart, different spacing is also contemplated. Additionally, more than two cutting wires can be provided, e.g. three cutting wires such as wires 180, 181, 182 of FIG. 4A, four cutting wires, etc. The three cutting wires 180, 181, 182, can be equidistantly spaced apart encircling tracking wire 190 as shown or spaced at different distances.

The device of the present invention functions to treat the stenotic lesion inside the vessel wall, thereby opening or enlarging the passageway in the vessel which was restricted. The stenosis can be a result of plaque buildup, endothelial growth, blood clots, etc. The device can also be used to treat other lesions restricting passageways in other body lumens.

With reference to FIGS. 1, 5 and 6C, the first cutting member is in the form of a wire 120 and has a distal portion 122 which is connected to a distal portion 142 of a tracking member in the form of a wire 140. In the illustrated embodiment, a distalmost tip 123 of the cutting wire 120 is attached to the tracking guidewire 140. Similarly, the second cutting member is in the form of a wire 130 and has a distal portion 132 which is connected to the distal portion 142 of the tracking member 140. In the illustrated embodiment, a distalmost tip 133 of the cutting wire 130 is attached to the tracking guidewire 140. One way of attachment of the wires 120, 130 to wire 140 is to twist the wires together. Other methods of attachment are also contemplated such as welding, bonding or placement of a separate element such as a collar, e.g. collar 145, over the end of the wires to frictionally engage the wires. The cutting wires 120, 130 remain unattached proximal of the distal connection to enable them to be separated from the tracking wire 140, e.g. moved transversely with respect to the longitudinal axis of the tracking wire 140. In FIGS. 6B and 6C, the initial position of the wires are shown; in FIGS. 6D and 6E the wires are separated as described in detail below.

A coil 157 can be provided at the tip such as illustrated in FIG. 1. Several marker bands 158 can be provided on tracking wire 140 for imaging. In the alternate embodiment of FIG. 1A, a shrink wrap 153 can be provided over the connection region of the tracking wire 140' and cutting wires 120', 130' of cutting assembly 110'. The cutting assembly 110' can also include a coil similar to coil 157 and a shrink wrap similar to shrink wrap 153.

Note the tracking wire and cutting wire can be of substantially the same length, both extending out of the body for reinsertion of a catheter over the tracking wire as described below. Alternatively, they can be of different lengths. The cutting member (wire) has a proximal portion and a distal portion, the proximal portion configured to extend outside the patient when the cutting member is positioned in the body lumen adjacent the lesion.

Various configurations of the cutting wires 120, 130 are illustrated to effectively treat lesions. In the embodiment of FIG. 1, the wires 120, 130 are substantially circular in cross-section until a transition region, i.e. region 125, where it transitions to a wire substantially triangular in cross section forming a V-shaped cutting surface 127 on a first surface opposite a second surface 129 facing the tracking wire 140 (FIG. 3). A concave or convex surface can be formed on one, two or all three sides (see e.g. wire 170 of FIG. 3A). A convex surface on the side opposite the cutting edge helps to conform to the outer surface of the catheter balloon.

Other cross-sectional shapes of the cutting wires 120, 130 are also contemplated, including but not limited to, polygonal shapes that are substantially: rectangular, square, trapezoidal (see e.g. wire 175 of FIG. 3B), hexagonal, pentagonal, octagonal, diamond shaped, etc. A round or oval wire cross-section with a sharpened surface is also contemplated. In the embodiment of FIG. 3C, a rhombus shaped wire 180 is illustrated. This shape facilitates cutting if the cutting wire is rotated. FIG. 3D illustrates a caltrop shape wire 184 configured so that one point will always point upward. FIG. 3E illustrates an upside down T-shape wire 188. The base of wire 188 can be convex.

It is contemplated that cutting wire 130 has the same configuration as cutting wire 120. However, in alternate embodiments, the cutting wire 130 can have an alternate configuration, including but not limited to, any of the foregoing cross-sectional wire shapes.

Note, if desired, only a portion of the cutting wires 120, 130 can have the cutting edge or surface, e.g. the distal region, with a remaining portion being atraumatic and non-cutting. This is illustrated in FIG. 2, where the circular cross-section at a more proximal region is atraumatic. Note a region distal of the cutting portion can be atraumatic, e.g. can transition back to a substantially circular cross-section.

One method of use of the wire assembly 110 of the present invention will now be described. Wire assembly 110' would be used in the same manner. Initially, a conventional angioplasty catheter 100 is inserted over a conventional guidewire G to the treatment site as shown in FIG. 6. Guidewire G extends through a lumen 102 in the catheter 100. Access to the vessel can be obtained through the femoral artery or vein for example. Note the proximal end of the catheter 100 and guidewire G extend outside the patient's body. The angioplasty catheter 100 has an inflatable balloon 104 which is in fluid communication with an inflation lumen of the catheter as is conventional. At the target site, inflation of the balloon 104 expands the balloon to expand the lesion B and widen the lumen of the vessel V.

If the stenotic lesion cannot be successfully opened by a conventional balloon due to lack of force, the wire assembly 110 (or 110') of the present invention can be utilized. In this case, the guidewire G is removed from the guidewire lumen 102 of the catheter 100 (see FIG. 6B) and the wire assembly 110 is inserted through the lumen 102 as shown in FIG. 6B. Thus, by insertion through the lumen 102, the tracking guidewire 140 and cutting wires 120, 130 of wire assembly 110 are inserted to the target site.

Next, the catheter 100 is removed from the treatment site and vessel, and removed from the body, leaving the wire assembly 110 at the target site as shown in FIG. 6C. The catheter 100 is then reinserted over the proximal end of tracking wire 140. Note that instead of reinserting the same catheter used in the step of FIG. 6, alternatively, a different balloon catheter can be inserted. In either event, the catheter 100 is inserted over the proximal portion of the tracking wire 140 such that the tracking wire 140 extends through the lumen 102; however, cutting wires 120 and 130 remain outside the lumen 102 as shown in FIG. 6D. In this manner, the tracking wire 140 provides a guide for the catheter 100 to the target site, while the cutting wires remain adjacent an outer surface of the catheter 100 for subsequent expansion into contact with the lesion. As shown in FIG. 6D, there is an increased gap 125 between the cutting wires 120, 130 and tracking wire 140 caused by the catheter 100 positioned between the tracking wire 140 and the two wires 120, 130.

To expand or move the cutting wires 120, 130 transversely with respect to the longitudinal axis of the tracking wire 140 (and transverse to the longitudinal axis of the catheter 100), the balloon 104 is inflated, forcing the cutting wires 120 and 130 into contact with the lesion B so the cutting edge or surface can treat the lesion. It should be appreciated that instead of a balloon, a mechanical expander or other structure can be used to force the cutting wires 120, 130 radially and into contact with the lesion. If desired, the balloon 104 can be deflated and the wire assembly easily rotated to another position for subsequent transverse movement of the cutting wires by the balloon into contact with another region of the lesion B to treat select portions of the stenosis.

As can be appreciated, the method described above utilizes the same catheter for the initial step (FIG. 6) as well as for the subsequent step of reinsertion for placement only over the tracking wire 140 (FIG. 6D). However, it is also contemplated that a different catheter can be used for reinsertion over only the tracking wire 140.

Also, as shown, a single balloon is utilized to expand both wires substantially simultaneously. It is also contemplated that a separate balloon or separate expansion of the single balloon can be used to move the wires 120, 130 independently/separately.

As can be appreciated, the wire assembly 110 can accommodate balloon catheters having relatively small guidewire lumens.

Also, although access is described through the femoral artery, other approaches to the target site are also contemplated. Additionally, although described for use to treat lesions in vessel lumens, it can also be used to remove other structures constricting the passageway in the vessel or in other body lumens.

The cutting and tracking components are illustrated as wires, but other structures for the cutting member and tracking member are also contemplated such as a hard plastic tube or a metal hypotube. The metal hypotube can be formed with a cutting surface or alternatively have a cutting member such as a cutting tube attached thereto.

The cutting wire assembly of the present invention as described can be used in various vessels including for example, veins such as the femoral veins, grafts such as dialysis grafts, etc. Other vessels are also contemplated such as use in carotid arteries, coronary arteries, the descending aorta and renal arteries, the external iliac and internal iliac arteries and the common femoral and deep femoral arteries. Applications for this device include, but are not limited to, treating stenotic venous and arterial anastomosis, lesions resistant to conventional angioplasty, stent restenosis, and vessels with buildup of intima, etc.

While the above description contains many specifics, those specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. A system for treating a lesion in body lumen to enlarge a passageway in the body lumen comprising:
   a catheter having a lumen and an expandable portion; and
   a cutting assembly including a plurality of cutting members and a tracking member, the tracking member attached to at least one of the cutting members, wherein the expandable portion of the catheter is expandable to move the cutting members in a direction transverse to a longitudinal axis of the tracking member, each of the cutting members having a proximal portion and a distal portion, the proximal portions extending outside the patient when the cutting members are positioned in the body lumen adjacent the lesion, the plurality of cutting members having a cutting surface configured to treat the lesion to enlarge the passageway in the body lumen when moved by the expandable portion of the catheter.

2. The system of claim 1, wherein at least one of the cutting members and the tracking member are connected at distal regions thereof.

3. The device of claim 1, wherein the tracking member has a coil at a distal end, and a shrink wrap is positioned over a connection region of the cutting member and tracking member.

4. The system of claim 1, wherein the cutting surface is substantially triangular in cross-section.

5. The device of claim 1, wherein the cutting members are wires and the tracking member is a wire.

6. The system of claim 1, wherein the cutting members have a first proximal portion of a first continuous configuration and a second distal portion of a second continuous configuration, the second portions including the cutting surface and the first portions being atraumatic.

7. The system of claim 6, wherein a height of the distal portion of the cutting members is less than a height of the proximal portion of the cutting members.

8. The system of claim 1, wherein the expandable portion comprises an inflatable balloon.

9. The system of claim 1, wherein the tracking member includes a plurality of marker bands.

10. The system of claim 1, wherein the cutting members have a second surface opposite the cutting surface the second surface facing the tracking member.

11. The system of claim 1, wherein the cutting members are circular in a region proximal of the cutting surface.

12. The system of claim 1, wherein the cutting members have a proximal region of a height greater than a height of a distal region, the cutting surface being at the distal region.

* * * * *